United States Patent [19]

Baldwin et al.

[11] 4,210,653

[45] Jul. 1, 1980

[54] PYRIDYLOXYPROPANOLAMINES

[75] Inventors: John J. Baldwin, Lansdale; David E. McClure, Hatfield, both of Pa.

[73] Assignee: Merck & Co., Inc., Rahway, N.J.

[21] Appl. No.: 919,593

[22] Filed: Jun. 27, 1978

[51] Int. Cl.$^2$ .................... A61K 31/44; C07D 213/04
[52] U.S. Cl. ................................. 424/263; 546/270; 546/330; 546/334
[58] Field of Search ................. 546/270, 330, 334; 424/263

[56] References Cited

U.S. PATENT DOCUMENTS 4,088,764   5/1978   Raabe et al. .................... 548/342

OTHER PUBLICATIONS

Kaiser et al., J. Med. Chem. 20, 687 (1977).

*Primary Examiner*—John M. Ford
*Assistant Examiner*—Robert C. Whittenbaugh
*Attorney, Agent, or Firm*—Daniel T. Szura; Harry E. Westlake, Jr.

[57] ABSTRACT

Pyridyloxypropanolamines, their preparation and use as antihypertensive agents is disclosed.

13 Claims, No Drawings

PYRIDYLOXYPROPANOLAMINES

BACKGROUND OF THE INVENTION

The present invention is concerned with aryloxypropanolamine compounds which have pharmaceutical utility.

Hydroxyphenyloxypropanolamine compounds having pharmaceutical activity are described in J. Med. Chem. 20, 687 (1977), Farmaco. Ed. Sci., 24, 349 (1969), Therapic 22, 1343 (1967), J. Med. Chem. 12, 638 (1969) and Acta. Pharm. Sci., 7, 551 (1970). Heterocycle oxypropanolamine compounds having pharmaceutical activity, e.g. β-adrenergic blackade, are disclosed in U.S. Pat. Nos. 4,000,282, 4,053,605, South Africa Pat. No. 741070 and Belgian Pat. No. 858,867.

Hydroxyphenyloxy-, unsubstituted pyridyloxy- and imidazopyridyloxypropanolamine compounds have been discovered. These compounds are useful for treating cardiovascular conditions such as angina pectors and hypertension.

SUMMARY OF THE INVENTION

Hydroxyphenoxypropanolamines, unsubstituted pyridyloxypropanolamines and imidazopyridyloxypropanolamines and their use as pharmaceuticals.

DESCRIPTION OF THE PREFERRED EMBODIMENTS

An embodiment of the present invention is compounds having the formula $$R_a-O-CH_2-CHOR-CH_2-NHR^1 \quad\quad I$$

pharmaceutically acceptable salts thereof wherein $R_a$ is

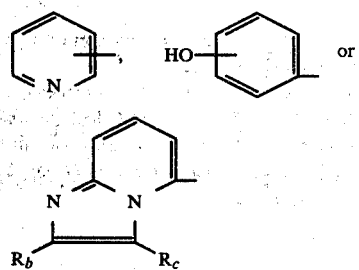

wherein $R_b$ and $R_c$ are H, $C_1-C_6$ alkyl, $SCF_3$, or Cl, or are jointed to form the aalkylene group $-(CH_2)_4-$, R is H or

wherein L is $C_1-C_{10}$ alkyl, phenyl or mono- or di-substituted phenyl wherein said substituents are $C_1-C_4$ alkyl, $C_1-C_4$ alkyl, $C_1-C_4$ alkoxy or halo and $R^1$ is a phenyl $C_2-C_6$ linear or branched alkyl group having the formula:

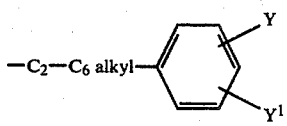

-continued

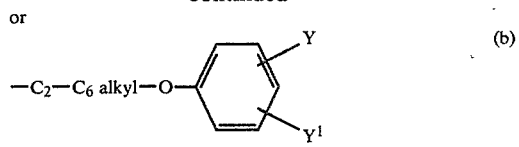

wherein
Y and $Y^1$, when separate, are H, $-OCH_3$, $-OH$, halo or CN and when joined, form

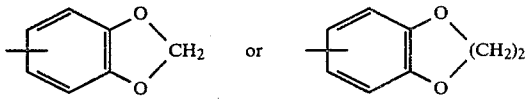

with the phenyl group.
R is H or the

group, with H being preferred. The L group includes $C_1-C_{10}$, linear and branched hydrocarbon alkyl such as methyl, n-decyl, tert butyl, isoamyl, n-heptyl and the like with $C_1-C_4$ alkyl being preferred, and phenyl or mono- and disubstituted phenyl such as tert butylphenyl, 2,6-dibromophenyl, 3-methylphenyl, 4-n-propylphenyl, 3,5-dimethoxyphenyl, 4-iodophenyl, 2-methyl-4-chlorophenyl, 4-fluorophenyl and the like, with monosubstituted phenyl preferred.

The $R^1$ phenyl $C_2-C_6$ group includes the branched and linear alkyl moieties. This linear alkyl group has 2-6 carbon atoms, with 2-4 carbon atoms being preferred and two carbon atoms being most preferred. The branched alkyl group has 2-6 carbon atoms with 3-5 carbon atoms being preferred. These $R^1$ groups are illustrated by the following formulae:

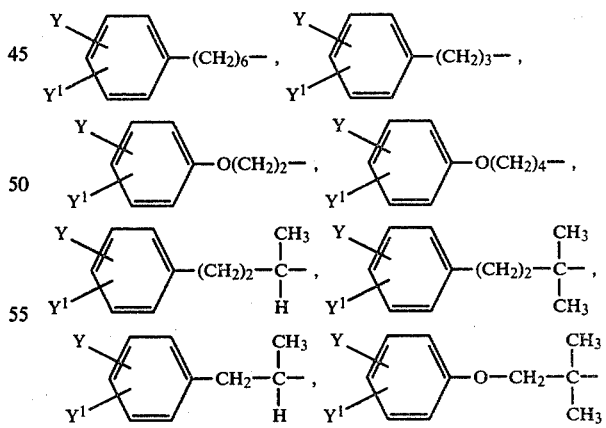

and the like.

Y and $Y^1$ may be H, $-OCH_3$, CN, $-OH$ or halo. The halo substituent includes Cl, Br, I or F with Cl and F being preferred.

Y and $Y^1$ may also be joined to form the dioxyalkylidene moiety $-O-(CH_2)_1$ or $_2-O-$ which is attached to the phenyl ring to form a bicyclic group of the formula:

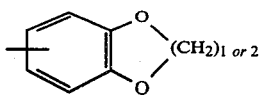

Preferred positioning of the dioxyalkylene moiety is

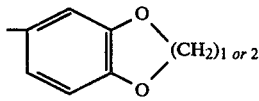

One class of preferred compounds has the formula

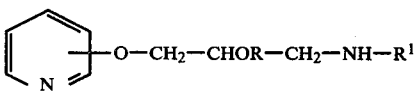

II

More preferred are the formula II compounds where R is H and $R^1$ has the formula

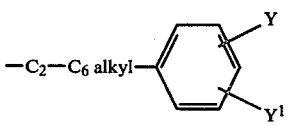

(a)

It is preferred that the (a) moiety be in the 2-position in the pyridine ring.

Another class of preferred compounds are those having the formula

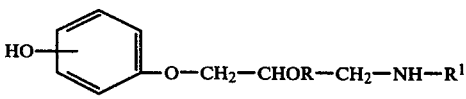

III

Preferred compounds of formula III are those where R is H. It is more preferred to have the —OH group in formula III meta or para to the propoxyamino group.

Another class of preferred compounds has the formula

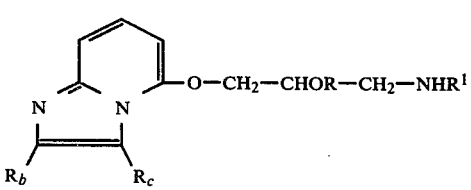

IV

Preferred compounds of formula IV are those where $R_b$ and $R_c$ substituents are H, $SCF_3$ and $C_1$—$C_3$ alkyl e.g. $CH_3$, isopropyl etc. or —$(CH_2)_4$—. A preferred $R^1$ group in the formula IV compounds has the formula

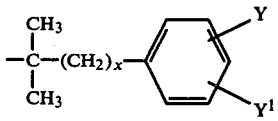

where x is 1 or 2 and especially where x is 2.

All the optical isomer forms, that is mixtures of enantiomers or diastereomers e.g. racemates as well as the individual enantiomers of formula I are included. These individual enantiomers of formula I are commonly designated according to the optical rotation they effect by (+) and (−), (L) and (D), (l) and (d) or combinations of these symbols. These isomers may also be designated according to their absolute spatial configuration by (S) and (R) which stand for sinister and rectus, respectively. Where no symbol is used in naming a compound, the compound is a racemate. The (S) isomer is a preferred isomer configuration.

The compounds of formula I have one chiral center at the 2-position in the propoxy substituent and can have a second chiral center when the alkylene group in $R^1$ is e.g.,

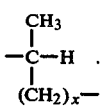

The aforesaid symbols e.g. (R), (S), or (R,S), when used to designate a formula I compound, refer only to the optical configurations around the chiral center at the 2-position in the propoxy substituent.

The compounds of the present invention can be prepared by any convenient process.

One such process involves the coupling of a haloheterocycle with a suitable substituted (i) oxazolidine and hydrolyzing the reaction product obtained or (ii) glycolamine. These processes are illustrating by the following reaction equations:

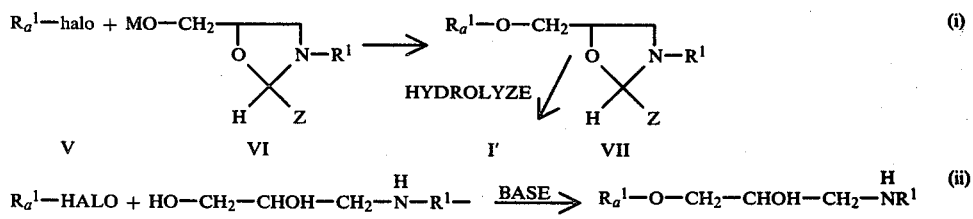

$R_{a'}$ is pyridyl or imidazopyridyl. Halo may be Cl, Br F and I, with Cl being preferred. M is an alkali metal, either potassium or sodium. Z can be hydrogen or the residue of any suitable aldehyde

e.g., an arylaldehyde, such as benzaldehyde, naphthaldehyde and the like, or an alkanol such as acetaldehyde, butyraldehyde and the like. The process for preparing oxazolidines where M is hydrogen is disclosed in U.S. Pat. Nos. 3,718,647 and 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this reaction (i) may also be carried out with in-situ formation of the alkali metal oxazolidine salt (Formula VI) by reacting the oxazolidine

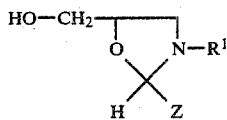
VIII with the formula V heterocycle in the presence of a strong base as used in reaction (ii) such as an alkali metal alkoxide (e.g., K—O—C—(CH$_3$)$_3$) or sodium hydride.

The coupling reactions can be carried out at temperatures ranging from about 0° C. to the reflux temperature of the solvent. A temperature range of about 10° C. to about 75° C. is preferred. The reaction is generally carried out in a solvent. Any suitable solvent may be used. Examples of useful solvents are dimethylformamide, dimethylsulfoxide, hexamethylphosphoramide, tert butanol, alkanols and the like. The hydrolysis is carried out using conventional acid hydrolysis reagent and techniques, e.g., treatment with a solution of an acid such as acetic acid or any strong mineral acid such as HCl or H$_2$SO$_4$. The hydrolysis product can be directly obtained as the salt of the acid used for the hydrolysis. Ordinarily, the product I$^1$ is recovered as the free base after conventional neutralization of the salt.

The coupling reaction is ordinarily carried out at atmospheric pressure. Higher pressures may be used if desired.

Where compounds of Formula I where R$_a$ is hydroxy phenyl are to be prepared via the (i) or (ii) coupling reactions, the V reactant must be R$_{a''}$—OH, where R$_{a''}$ is hydroxy phenyl or the aforesaid protected moiety and (a) the VI oxazolidine must be

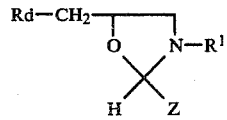

or (b) the glycolamine must be Rd—CH$_2$—CHOH—CH$_2$—NR$^1$, where Rd is alkyl or aryl sulfonyloxy such as phenylsulfonyloxy C$_1$-C$_6$ alkylphenylsulfonyloxy, p-methylphenylsulfonyloxy, naphthylsulfonyloxy, C$_1$-C$_{10}$ alkylsulfonyloxy, methylsulfonyloxy, decylsulfonyloxy and the like. The reaction conditions using the R$_{a''}$—OH and the sulfonyloxy derivatives are substantially the same as far as the (ii) reaction, namely in the presence of a strong base, at temperatures, pressures and in solvents, as described above.

When a racemic oxazolidine is used as a reactant, the product is obtained as a racemate. The racemate may be separated into its individual enantiomers by conventional resolution techniques, e.g., using an enantiomer of a suitable optically active organic acid such as tartaric acid.

When Z in the oxazolidine i.e. Formula VI, VII or VIII, is other than hydrogen, in addition to the chiral center at oxazolidine position 5 there is a second chiral center at position 2. However, whenever the oxazolidine is designated e.g. as (S), (R) or (R,S), this designation refers only to the optical configuration around the carbon atom at the 5 position.

By using a single optical isomer of said oxazolidine or of said glycolamine, the product may be obtained directly as a single enantiomer. Thus, if the S-isomer of the oxazolidine is used, then the product obtained will be the S-isomer. This provides a convenient way for directly preparing individual isomers of the present pyridines.

Another convenient process for preparing the present compound is by treating an appropriate substituted epoxide with a suitable amino as illustrated by the following reaction equation:

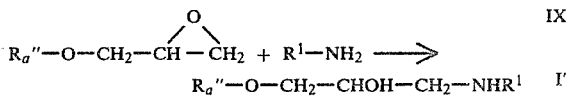

R$_{a''}$ is hydroxyphenyl or a protected moiety e.g. benzyloxyphenyl. This reaction is advantageiously carried out in excess amine (R$^1$NH$_2$) reactant. Temperatures up to reflux can be used. An especially useful raction temperature range is room temperature to about 100° C. The reaction is conveniently carried out at room temperature.

The product from the epoxide/R$^1$NH$_2$ reaction is ordinarily a racemate, and can be separated using conventional resolution procedures.

If a single optical isomer of the formula IX epoxide is used, as the reactant, the product obtained is the corresponding single optical isomer e.g.

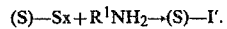
(S)—Sx+R$^1$NH$_2$→(S)—I'.

The optically active epoxide intermediates of formula IX can be prepared according to the reaction illustrated below:

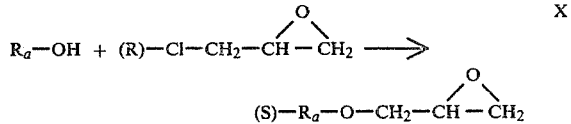

Conventional reaction conditions are used. Conversely, if the (S) isomer of formula X is used, the corresponding (R) isomer of formula XI is obtained. Preparation of the intermediates will be shown in the examples below.

The compounds of the present invention have β-adrenergic blocking activity. This β-adrenergic blocking activity is determined by measuring the ability of representative pyridines to block the β-adrenergic stimulant effect of isoproterenol in a test animal.

The present compounds generally exhibit antihypertensive activity of immediate onset. This rapid onset antihypertensive activity is determined by administering a representative compound of the present invention to spontaneously hypertensive (SH) rats and measuring the effect on blood pressure. The present compounds also exhibit random α-adrenergic blocking activity.

This α-adrenergic blocking activity is determined (a) in-vitro by measuring a present compound's ability to displace radio-labeled α-antagonist from a tissue substrate or (2) in-vivo, by determining the ability of a present compound to counteract the α-stimulant effects of phenylephrine.

Where the present compounds show the ability to reduce blood pressure in the SH rat, it indicates that the compounds and their salts may be useful to treat essential hypertension in humans.

The β-adrenergic blocking effectiveness of the present compounds indicates that they are useful in treating human cardiovascular conditions such as angina pectoris and arrhythmias.

Where compounds also have α-adrenergic blocking activity, they may also be useful for treating hypertension which results from pheochromocytoma.

For use as β-or α/β-adrenergic blocking agents. and/or antihypertensive agents, the compounds of the present invention can be administered orally, by inhalation, by suppository or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present pyridine) to compounding ingredients will vary as the dosage form requires. Conventional procedures are used to prepare the pharmaceutical formulations.

The effective daily dosage level for the present compounds may be varied from about 100 mg. to about 3000 mg. Daily doses ranging from about 200 to about 2500 mg. are preferred, with about 300 to about 1000 mg. being a more preferred range. Oral administration is preferred. Either single or multiple daily doses may be administered depending on unit dosage.

Thus, another embodiment of this invention is a pharmaceutical composition containing a therapeutically effective amount of a compound of the present invention.

The following examples illustrate the preparation of representative compounds of the present invention. Temperatures are in °Celsius.

EXAMPLE 1

1-(1-methyl-3-phenylpropylamino)-3-(4-hydroxyphenoxy)-2-propanol hydrochloride

A mixture of 1.28 g. (5 mmole) of 1-(2,3-epoxy-1-propoxy)-4-benzyloxybenzene and 2.2 g. (15 mmole) of 1-methyl-3-phenylpropylamine was heated at 90° C. for 2½ hours. The mixture was triturated with hexane, and the hexane decanted. The phenolic benzyl ether of the title compound was crystallized from ether to give 1.30 g. of the free base (64%); mp 71°–74° C.

Hydrogenolysis of the benzyl ether from above was accomplished in 100 ml. ethanol using 5% Pd/C under 30 psi of hydrogen pressure. After filtration and concentration, the hydrochloride salt was prepared in ethanol/ether. Recrystallization from 2-propanol gave 1-(1-methyl-3-phenylpropylamino)-3-(4-hydroxyphenoxy)-2-propanol hydrochloride (30%); mp 183°–187° C.

EXAMPLE 2

1-(3-phenylpropylamino)-3-(4-hydroxyphenoxy)-2-propanol hydrochloride

Using the procedure described in Example 1 and substituting 3-phenylpropylamine for 1-methyl-3-phenylpropylamine, a 31% overall yield of 1-(3-phenylpropylamino)-3-(4-hydroxyphenoxy)-2-propanol hydrochloride (mp 150°–153° C.) was obtained.

EXAMPLE 3

(a) 1-methyl-3-(4-chlorophenyl) propylamine

To 36.5 g. (0.2 mole) of 4-(4-chlorophenyl)-2-butanone and 77 g. (1 mole) of ammonium acetate in 400 ml. of methanol was added 6.3 g. (0.1 mole) of sodium cyanoborohydride, and the mixture was stirred at room temperature for 3 days. Concentrated HCl was added to a pH of ≦2. The solvent was stripped, water was added, and then washed with ether. The aqueous solution was made alkaline with KOH pellets (pH>10). After extraction into methylene chloride and concentration, distillation of the residue gave 18.2 g. (50%) of 1-methyl-3-(4-chlorophenyl)propylamine; bp 90°–95°/0.1 mm.

(b) 1-methyl-3-(4-cyanophenyl)propylamine

Using the procedure of Example 3 (a) with 4-(4-cyanophenyl)-2-butanone in place of 4-(4-chlorophenyl)-2-butanone, distillation under reduced pressure gave 1-methyl-3-(4-cyanophenyl)propylamine (b.p. 106°–112°/0.2 mm).

(c) 4-(2,3-epoxy-1-propoxy)-phenol

To an ice-cooled solution of 55 g. (0.5 mole) of hydroquinone and 46 g. (0.5 mole) of epichlorohydrin in 900 ml. of water was added an ice-cooled solution of 20 g. (0.5 mole) of sodium hydroxide in 900 ml. of water. The mixture was allowed to stand at 0° C. for 3 days. After washing with ether, the solution was added to 72 g. of sodium hydroxide in 4 l. of water and stored at 10° C. for 3 hours. The solution was saturated with ammonium carbonate and extracted with chloroform. After drying (Na₂SO₄) and concentrating the chloroform, the residual oil was predominantly 4-(2,3-epoxy-1-propoxy)-phenol (23%) which was used in later step without further purification.

(d)
1-(1-methyl-2-phenoxyethylamino)-3-(3-hydroxyphenoxy)-2-propanol

A mixture of 1.66 g. (10 mmole) of 3-(2,3-epoxy-1-propoxy)-phenol and 4.5 g. (30 mmole) of 1-methyl-2-phenoxyethylamine was heated at 80° C. overnight. The mixture was taken up in ether, and hexane was added to precipitate the product. Recrystallization from ethyl acetate gave 1-(1-methyl-2-phenoxyethylamino)-3-(3-hydroxyphenoxy)-2-propanol (38%); mp 124°–127° C.

Following essentially this procedure of Example 3(d) the following compounds were prepared using an appropriate amine reactant as indicated.

| Ex. | $R^1NH_2$ Amine Reactant | Recryst. Solvent | Product | M.P. °C |
|---|---|---|---|---|
| 4 | ⟨phenyl⟩—(CH$_2$)$_2$—CH(CH$_3$)—NH$_2$ | benzene | ⟨phenyl(HO)⟩—O—CH$_2$—CH(OH)—CH$_2$—N(H)—CH(CH$_3$)—(CH$_2$)$_2$—⟨phenyl⟩ | 112–118 |
| 5 | CH$_3$O—⟨phenyl⟩—(CH$_2$)$_2$—CH(CH$_3$)—NH$_2$ | CH$_3$CN | ⟨phenyl(HO)⟩—O—CH$_2$—CH(OH)—CH$_2$—N(H)—CH(CH$_3$)—(CH$_2$)$_2$—⟨phenyl⟩—OCH$_3$ · HCl | 172–176 |
| 6 | NC—⟨phenyl⟩—(CH$_2$)—CH(CH$_3$)—NH$_2$ | acetone | ⟨phenyl(HO)⟩—O—CH$_2$—CH(OH)—CH$_2$—N(H)—CH(CH$_3$)—CH$_2$—⟨phenyl⟩—CN · HCl | 183–186 |

EXAMPLE 7

1-(1-methyl-2-phenoxyethylamino)-3-(4-hydroxyphenoxy)-2-propanol

A mixture of 1.66 g. (10 mmole) of 4-(2,3-epoxy-1-propoxy)-phenol and 4.5 g. (30 mmole) of 1-methyl-2-phenoxyethylamine was heated at 90° C. for 3 hours. The residue was triturated with ether and filtered. Recrystallization from ethyl acetate to which a little methanol was added gave 1-(1-methyl-2-phenoxyethylamino)-3-(4-hydroxyphenoxy)-2-propanol; mp 173°–175° C.

Following essentially the same procedure as in Example 7, the following compounds were also prepared, using the appropriate $R^1NH_2$ reactant as indicated.

(b)
2-[3-(1,1-dimethyl-3-phenylpropylamino)-2-hydroxy-1-propoxy]pyridine maleate A solution of 3.9 g. (16 mmole) 3-(1,1-dimethyl-3-phenylpropyl)-1,2-dihydroxypropane, 15 ml. benzaldehyde, 9 ml. benzene, and 100 mg. benzoic acid was refluxed for 16 hours while a Dean=Stark trap was being used to collect the water. The solution was diluted with benzene and washed with aqueous potassium carbonate. The mixture was concentrated and the residue was distilled under reduced pressure (0.4 mm.) at a pot temperature of 75°–80° C. The residue from above in 50 ml. DMF was then added dropwise to sodium hydride (1.0 g. of a 50% oil dispersion washed with

| Ex. | $R^1NH_2$ reactant | Recryst. Solvent | Product | M.P. °C |
|---|---|---|---|---|
| 8 | CH$_3$O—⟨phenyl⟩—(CH$_2$)$_2$—CH(CH$_3$)—NH$_2$ | CH$_3$CN | HO—⟨phenyl⟩—O—CH$_2$—CH(OH)—CH$_2$—N(H)—CH(CH$_3$)—(CH$_2$)$_2$—⟨phenyl⟩—OCH$_3$ · HCl | 171–181 |
| 9 | Cl—⟨phenyl⟩—(CH$_2$)$_2$—CH(CH$_3$)—NH$_2$ | EtOAc/CH$_3$OH | HO—⟨phenyl⟩—O—CH$_2$—CH(OH)—CH$_2$—N(H)—CH(CH$_3$)—(CH$_2$)$_2$—⟨phenyl⟩—Cl · HCl · ½H$_2$O | 175–183 |
| 10 | NC—⟨phenyl⟩—(CH$_2$)$_2$—CH(CH$_3$)(NH$_2$) | Acetone/CH$_3$CN | HO—⟨phenyl⟩—O—CH$_2$—CH(OH)—CH$_2$—N(H)—CH(CH$_3$)—(CH$_2$)$_2$—⟨phenyl⟩—CN · HCl | 176–181 |

EXAMPLE 11

(a)
3-(1,1-dimethyl-3-phenylpropylamino)-1,2-dihydroxypropane

To 1,1-dimethyl-3-pehnylpropylamine (3.6 g., 22 mmole) in 20 ml. 2-propanol at 50° C. in an oil bath was added glycidol (1.7 g., 23 mmole) in 10 ml. 2-propanol dropwise over 5–10 min. The mixture was heated at 75° C. for 2 hours. After evaporation of the solvent, vacuum distillation provided 3.9 g. (75%) of 3-(1,1-dimethyl-3-phenylpropylamino)-1,2-dihydroxypropane (bp 160°–180°/0.5 mm) which crystallized upon standing (mp 74°–77° C.).

hexane) in 25 ml. DMF. After the addition, stirring was continued for 1 hour. 2-Chloropyridine (1.80 g., 16 mmole) in 25 ml. DMF was added and the mixture heated at 70° C. for 16 hours. Most of the DMF was evaporated. Water and ether were added and the layers separated. The ether solution was washed twice with 100 ml. 4N HCl and the combined acid washings were heated on a steam bath for ½ hour. After washing with ether, the aqueous phase was made basic with KOH. The oil was extracted with CH$_2$Cl$_2$, dried (Na$_2$SO$_4$), and concentrated to give 3.0 g. (60%) of the crude free base. A small sample was used to prepare the maleate salt in 2-propanol/ether, and recrystallization of this from 2-propanol gave pure 2-[3-(1,1-dimethyl-3-phenylpropylamino)-2-hydroxy-1-propoxy]pyridine maleate; mp 144°–146° C.

EXAMPLE 12

4-[3-(1,1-dimethyl-3-phenylpropylamino)-2-hydroxy-1-propoxy]pyridine dihydrochloride Using the same procedure as described in Example 11(b), but substituting 4-chloropyridine (0.9 g. 8 mmole) for 2-chloropyridine, 2.0 g. (80%) of the corresponding crude free base was obtained. The dihydrochloride salt was prepared in ethanol/ether and recrystallization of this gave pure 4-[3-(1,1-dimethyl-3-phenylpropylamino)-2-hydroxy-1-propoxy]pyridine dihydrochloride; mp 191°–193° C.

EXAMPLE 13

3-[3-(1,1-dimethyl-3-phenylpropylamino)-2-hydroxy-1-propoxy]pyridine dihydrochloride A solution of 2.4 g. (10 mmole) 3-(1,1-dimethyl-3-phenylpropylamino)-1,2-dihydroxypropane, 15 ml. benzaldehyde, 9 ml. benzene, and 100 mg. benzoic aicd was refluxed for 16 hours while a Dean-Stark trap was being used to collect the water. The solution was diluted with benzene and washed with aqueous potassium carbonate. The mixture was concentrated and the residue was distilled under reduced pressure (0.4 mm.) at a pot temperature of 75°–80° C.

To an ice-cooled solution of the residue from above in 10 ml. pyridine was added 1.15 g. methanesulfonyl chloride (10 mmole) dropwise of a few minutes. Stirring was continued at r.t. for 3 hours. Potassium carbonate (1.4 g., 10 mmole) in 50 ml. water was added, and the mixture was stripped on the rotary evaporator to remove pyridine. Extraction with $CH_2Cl_2$ and concentration gave the crude mesylate.

To 0.6 g. sodium hydride (50% oil dispersion) washed with hexane) in 10 ml. DMF was added 0.95 g. of 3-hydroxypridine (10 mmole) in 25 ml. DMF dropwise. Stirring was continued for 1 hour after completion of the addition. The crude mesylate from above in 15 ml. DMF was then added, and the mixture was heated at 100° C. for 16 hours. The mixture was cooled, and most of the DMF was stripped from the reaction mixture. Water was added and then washed with ether. The ether layer was washed twice with 50 ml. 3N HCl, and the combined acid washings were heated on a steam bath for ½ hour. After extraction with ether, the aqueous solution was made basic with $K_2CO_3$. Extraction with $CH_2Cl_2$, drying ($Na_2SO_4$), and concentration provided 2.3 g. (73%) of the crude free base.

A gradient elution chromatography of this material on Silica gel eluting with methanol/chloroform saturated with ammonia led to elution of the desired product with 3% methanol/chloroform saturated with ammonia. The dihydrochloride salt was prepared in ethanol/ether, and recrystallization from ethanol/ether gave pure 3-[3-(1,1-dimethyl-3-phenylpropylamino)-2-hydroxy-1-propoxy]pyridinine dihydrochloride, 225°–227° C.

EXAMPLE 14

2-[3-(1,1-dimethyl-3-phenylpropylamino)-2-hydroxy-1-propoxy]pyridine maleate A solution of 3.9 g. (16 mmole) 3-(1,1-dimethyl-3-phenylpropylamino)-1,2-dihydroxypropane, 15 ml. benzaldehyde, 9 ml. benzene, and 100 mg. benzoic acid was refluxed for 16 hours while a Dean-Stark trap was being used to collect the water. The solution was diluted with benzene and washed with aqueous potassium carbonate. The mixture was concentrated and the residue was distilled under reduced pressure (0.4 mm.) at a pot temperature of 75°–80° C. The residue from above in 50 ml DMF was then added dropwise to sodium hydride (1.0 g. of a 50% oil dispersion washed with hexane) in 25 ml. DMF. After the addition, stirring was continued for 1 hour. 2-Chloropyridine (1.80 g., 16 mmole) in 25 ml. DMF was added and the mixture heated at 70° C. for 16 hours. Most of the DMF was evaporated. Water and ether were added and the layers separated. The ether solution was washed twice with 100 ml. 4N HCl and the combined acid washings were heated on a steam bath for ½ hour. After washing with ether, the aqueous phase was made basic with KOH. The oil was extracted with $CH_2Cl_2$, dried ($NA_2SO_4$), and concentrated to give 3.0 g. (60%) of the crude free base. A small sample was used to prepare the maleate salt in 2-propanol/ether, and recrystallization of this from 2-propanol gave pure 2-[3-(1,1-dimethyl-3-phenylpropylamino)-2-hydroxy-1-propoxy]pyridine maleate, mp 144°–146° C.

EXAMPLE 15

(a) 3-Chloro-5-bromoimidazo[1,2a]pyridine

A suspension of 5-bromoimidazo-[1,2a] pyridine (6.0 g., 0.031 mol.) and 5 g. N-chlorosuccinimide in 50 ml. carbon tetrachloride is heated to the boiling point for 20 minutes, cooled, and filtered. The filtrate is concentrated under vacuum to a dark solid which is dissolved in boiling ethanol. The ethanol solution is treated with charcoal, filtered, and the cooled filtrate chromatographed on 75. g. silica gel. The 3-chloro-5-bromoimidazo[1,2a] pyridine (4.5 g.) is eluted with chloroform and purified by sublimation, m.p. 99°–101° C.

(b) 3-Trifluromethylthio-5-bromo-imidazo[1,2a]pyridine

A solution of 14.1 g. (0.072 mol.) of 5-bromoimidazo[1,2a]pyridine in 90 ml. tetrahydrofuran is stirred at −10° C. under nitrogen and treated with a steam of gaseous $CLSCF_3$ distilled from an ampoule. The mildly exothermic reaction is maintained 1 hour at −10° −0°, warmed cautiously to +10° and then room temperature, and filtered. The cake is recrystallized from absolute ethanol to give 4.0 g. white, solid hdyrochloride of 3-trifluoromethylthio-5-bromoimidazo[1-,2a]pyridine compound, m.p. 205°–206° C.

The 3-trifluoromethylthio-5-bromo-imidazo [1,2a]-pyridine base is obtained from the hydrochloride by extraction from aqueous sodium carbonate with $CH_2CL_2$ and sublimation of the residue from evaporation of the extracts to give 1.5 g. crystals, m.p. 59°–60° C.

(c) 2,3-Dimethyl-5-bromoimidazo[1,2a]pyridine

A mixture of 10.4 g. (0.060 mol.) of 6-bromo-2-aminopyridine and 9.0 g. (0.06 mol.) of 3-bromo-2-butanone in 40 ml. ethanol is refluxed 6 hours and then kept 18 hours at room temperature. The mixture is diluted with four volumes of ether to precipitate the hydrobromide of 2,3 dimethyl-5-bromoimidazo[1,2a] pyridine, 6.0 g., m.p. 270°–272°. The 2,3-dimethyl-5-bromoimidazo-[1,2a]pyridine, 4.4 g., m.p. 69°–71°, is obtained by partitioning the crude hydrobromide between chloroform and aqueous sodium carbonate and sublimation of the $CHCL_3$ soluble material.

(d) 1-Bromo-6,7,8,9-tetrahydropyrido[1,2a]benzimidazole .HBr

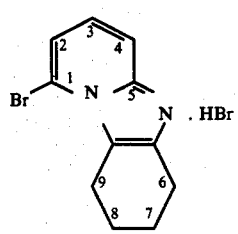

Similarly 2-chlorocyclohexanone (4.0 g., 0.03 mol.) is reacted with 6-bromo-2-aminopyridine (5.2 g., 30 mol.) in 30 ml. isopropanol for 18 hours at reflux to give 4.7 g. of white crystals of 1-bromo-6,7,8,9-tetrahydropyridoimidazo-[1,2a]benzimidazole hydrobromide, m.p. 268°–269° C., after treatment with 4 ml. of 48% aqueous hydrobromic acid.

(e) 2,3-dimethyl-5-[3-(1,1-dimethyl-3-phenylpropylamino)-2-hydroxy-1-propoxy]-imidazo-[1,2-$a$]-pyridinedihydrochloride Using the same procedure as described in Example 14 but substituting 2,3-dimethyl-5-bromoimidazo-[1,2-a]-pyridine (3.25 g., 10 mmole) for 2-chloropyridine and stirring at room temperature overnight instead of heating, 1.6 g. (42%) of the free base of the title compound was obtained after chromatography on silica gel eluting with 5% methanol/chloroform. The dihydrochloride salt was prepared in ethanol/ether, and recrystallization from 2-propanol gave pure 2,3-dimethyl-5-[3-(1,1-dimethyl-3-phenylpropylamino)-2-hydroxy-1-propoxy]-imidazo-[1,2-a]pyridinedihydrochloride; mp 206°–208° C.

Claims to the invention follow.
What is claimed is:

1. Compounds having the formula

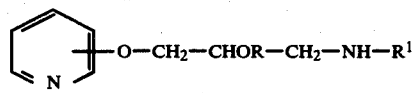

wherein R is H or

wherein
L is $C_1$–$C_{10}$ alkyl, phenyl or mono- or di-substituted phenyl wherein said substituents are $C_1$–$C_4$ alkyl, $C_1$–$C_4$ alkoxy or halo and
$R^1$ is a phenyl $C_2$–$C_6$ alkyl group having the formula

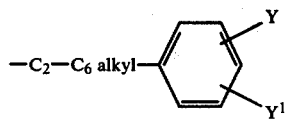

or

-continued

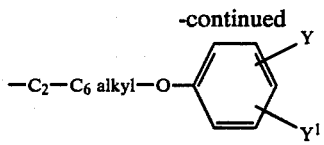

wherein Y and $Y^1$ are H, —$OCH_3$, —OH, halo or CN, or are joined to form —O—$(CH_2)_{1\ or\ 2}$—O—.

2. Compounds of claim 1 wherein R is

3. Compounds of claim 1 wherein R is H.
4. Compounds of claim 3 wherein $R^1$ is (b).
5. Compounds of claim 3 wherein $R^1$ is (a).
6. Compounds of claim 5 having the formula

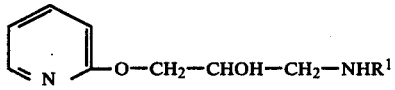

7. Compound of claim 6 wherein

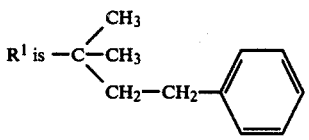

8. Compound of claim 6 wherein

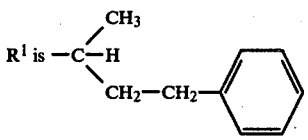

9. Compound of claim 6 having the S-isomer configuration.
10. Pharmaceutical composition for treating hypertension containing a therapeutically effective amount of a compound of claim 1.
11. Method of treating hypertension in humans which comprises administering an effective amount of a compound of claim 1.
12. Compounds of claim 5 having the formula

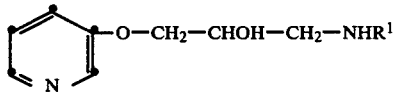

or

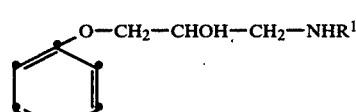

13. Compound of claim 12 wherein $R^1$ is

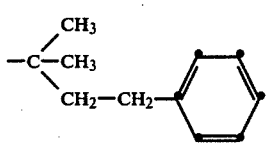

* * * * *